United States Patent [19]
Wright

[11] Patent Number: 5,233,991
[45] Date of Patent: Aug. 10, 1993

[54] METHOD AND APPARATUS FOR ESTIMATING OXYGEN SATURATION OF BLOOD USING MAGNETIC RESONANCE

[75] Inventor: Graham A. Wright, Palo Alto, Calif.

[73] Assignee: Board of Trustees of the Leland Stanford Junior University, Stanford, Calif.

[21] Appl. No.: 742,249

[22] Filed: Aug. 8, 1991

[51] Int. Cl.[5] ............................................. A61B 5/055
[52] U.S. Cl. ................................ 128/653.2; 128/653.3
[58] Field of Search ......................... 128/653.1–653.5; 324/306–309, 312, 318, 321

[56] References Cited

U.S. PATENT DOCUMENTS 4,775,522 10/1988 Clark, Jr. ...................... 128/653.4 X
4,984,574 1/1991 Goldberg et al. ................. 128/653.2

OTHER PUBLICATIONS

John M. Gomori, et al., "NMR Relaxation Times of Blood: Dependence on Field Strength, Oxidation State, and Cell Integrity," *Journal of Computer Assisted Tomography*, 11(4): 684–690, Jul./Aug. ©1987 Raven Press, N.Y.

K. R. Thulborn, et al., "Proton Imaging for in Vivo Blood Flow and Oxygen Consumption Measurements," *Journal of Magnetic Resonance*, 45, 188–191 (1981). Copyright ©1981 by Academic Press, Inc.

Keith R. Thulborn, et al., "Oxygenation Dependence of the Transverse Relaxation Time of Water Protons in Whole Blood at High Field," *Biochimica et Biophysica Acta*, 714 (1982) 265–270 ©Elsevier Biomedical Press.

G. A. Wright, et al., "Estimating Oxygen Saturation of Blood in vivo with MRI at 1.5T," *Society of Magnetic Resonance in Medicine*, (Works in Progress) Ninth Annual Scientific Meeting and Exhibition Aug. 18–24, 1990 New York, N.Y. USA.

Graham A. Wright, et al., "Estimating Oxygen Saturation of Blood in Vivo with MR Imaging at 1.5T[1]," *JMRI*, vol. 1 No. 3 275–284, May/Jun. 1991 ©SMRI, 1991.

*Primary Examiner*—Francis Jaworski
*Attorney, Agent, or Firm*—Townsend and Townsend Khourie and Crew

[57] ABSTRACT

The oxygen saturation of blood is determined by obtaining spin-spin relaxation time ($T2_b$) of the fluid using magnetic resonance imaging techniques. A simplified model relates oxygen saturation of blood to measured spin-spin relaxation time. A pulse sequence is given for in vivo estimation of $T2_b$ including a plurality of 180° refocusing RF signals which are equally spaced in time. The last refocusing pulse is slice selective. Fat signal is suppressed by initially using a short inversion recovery sequence followed by a frequency selective 90° pulse that excites only water protons.

15 Claims, 7 Drawing Sheets

METHOD AND APPARATUS FOR ESTIMATING OXYGEN SATURATION OF BLOOD USING MAGNETIC RESONANCE

BACKGROUND OF THE INVENTION

This invention relates generally to the use of magnetic resonance imaging for determining properties of moving fluids such as oxygen saturation of blood, for example, and more particularly the invention relates to determining blood oxygen saturation or other property based on the spin-spin relaxation time (T2) of the fluid.

Nuclear magnetic resonance (NMR) imaging, also called magnetic resonance imaging (MRI), is a non-destructive method for the analysis of materials and represents a new approach to medical imaging. It is completely non-invasive and does not involve ionizing radiation. In very general terms, nuclear magnetic moments are excited at specific spin precession frequencies which are proportional to the local magnetic field. The radio-frequency signals resulting from the precession of these spins are received using pickup coils. By manipulating the magnetic fields, an array of signals is provided representing different regions of the volume. These are combined to produce a volumetric image of the nuclear spin density of the body.

A descriptive series of papers on NMR appeared in the June 1980 issue of the IEEE Transactions on Nuclear Science, Vol. NS-27, pp. 1220–1225. The basic concepts are described in the lead article, "Introduction to the Principles of NMR," by W. V. House, pp. 1220–1226, which employ computed tomography reconstruction concepts for reconstructing cross-sectional images. A number of two-and three-dimensional imaging methods are described. Medical applications of NMR are discussed by Pykett in "NMR Imaging in Medicine,": Scientific American, May 1982, pp. 78–88, and by Mansfield and Morris, NMR Imaging in Biomedicine, Academic Press, 1982.

Briefly, a strong static magnetic field is employed to line up atoms whose nuclei have an odd number of protons and/or neutrons, that is, have spin angular momentum and a magnetic dipole moment. A second RF magnetic field, applied as a single pulse transverse to the first, is then used to pump energy into these nuclei, flipping them over, for example to 90° to 180°. After excitation the nuclei gradually return to alignment with the static field and give up the energy in the form of weak but detectable free induction decay (FID). These FID signals are used by a computer to produce images.

The excitation frequency, and the FID frequency, is defined by the Larmor relationship which states that the angular frequency, $\omega_0$, and the so-called magnetogyric ratio, $\gamma$, a fundamental physical constant for each nuclear species:

$$\omega_0 = B_0 \cdot \gamma$$

Accordingly, by superimposing a linear gradient field, $B_z = z \cdot G_z$, on the static uniform field, $B_0$, which defines the Z axis, for example, nuclei in a selected X-Y plane can be excited by proper choice of the frequency spectrum of the transverse excitation field applied along the X or Y axis. Similarly, a gradient field can be applied in the X-Y plane during detection of the FID signals to spatially localize the FID signals in the plane. The angle of nuclei spin flip in response to an RF pulse excitation is proportional to the integral of the pulse over time.

The spins of excited nuclei have two relaxation times associated therewith. The spin-lattice relaxation time, T1, is equivalent to the recovery time for spins in re-aligning with the longitudinal magnetization. The spin-spin relaxation time T2, depends on the decay of the transverse component of the magnetization. Both relaxation times are tissue specific.

Thulborn, et al., "Oxygenation Dependence of the Transverse Relaxation Time of Water Proteins in Whole Blood at High Field," *Biophysica Acta* 714, pp. 265–270, 1982 reported that the oxygen saturation of blood affected the T2 of the blood for in vitro experiments. However, for in vivo applications the motions of the body and/or of blood itself can adversely affect measurements of magnet resonance signals. Further, a more accurate model is required for correlating measurements of T2 and the corresponding values of blood oxygen saturation for experimental conditions used on in vivo measurement, in people.

The present invention is directed to a method and apparatus for determining the T2 relaxation time of vascular blood (in situ) and estimating oxygen saturation in the blood. The invention is applicable in other systems involving moving fluids wherein magnetic resonance signals are indicative of properties of the fluids.

SUMMARY OF THE INVENTION

Accordingly, an object of the invention is MRI apparatus for use in determining a specific property of a moving fluid based on the spin-spin relaxation time of the fluid which is determined by well-known methods from a series of measurements (at least 2) taken at different delays or echo times (TE) after the initial excitation.

Another object of the invention is a method of determining a fluid property such as oxygen saturation of blood.

A feature of the invention is the use of final section-selective 180° pulse before a single readout of the pulse echo per excitation where the time between the pulse and the echo is kept constant for measurements at different TE.

Another feature of the invention is the use of a train of 180° pulses between the excitation and the final 180° that regularly refocus all fluid MRI signals that could end up in the section of interest at data acquisition. The pulses in the train are equally spaced. To adjust TE for different measurements, different numbers of pulses are used (e.g. 0, 1, 2, 4 . . . ), or different spacings of pulses are used.

In accordance with one embodiment for obtaining oxygen saturation of blood, a simplified Luz-Meiboom model for the oxygen saturation of blood (%HbO$_2$) based on measured spin-spin relaxation time is established by using in vitro measurements to establish model constants for a particular subject. Thereafter, in vivo measurements of spin-spin relaxation time will result in a corresponding value of oxygen saturation of blood based on the model.

The invention and objects and features thereof will be more readily apparent from the following detailed description and appended claims when taken with the drawings.

DETAILED DESCRIPTION OF THE ILLUSTRATIVE EMBODIMENTS

Figure 1A:
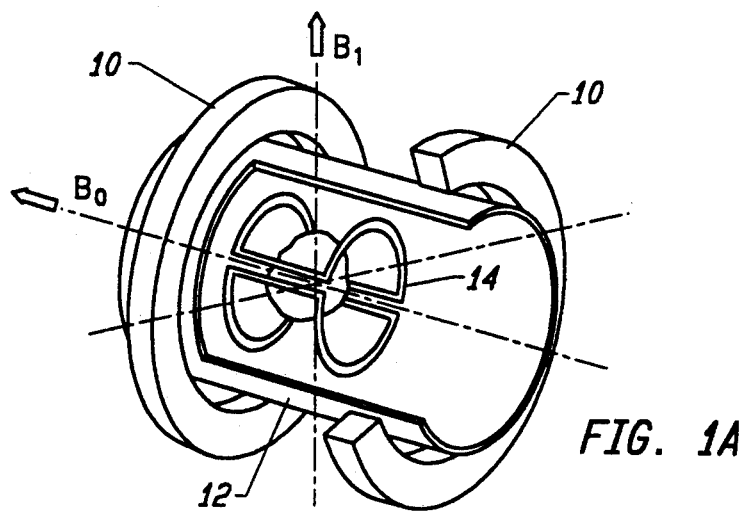
FIGS. 1A, 1B, 1C, and 1D illustrate the arrangement of conventional MRI apparatus and magnetic fields generated therein.
Figures 1B, 1C, 1D:
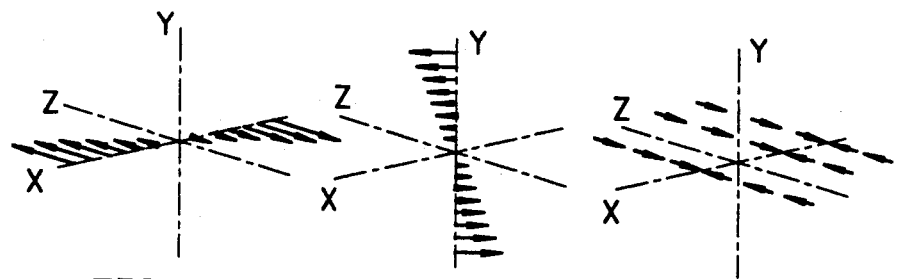

Referring now to the drawings, FIG. 1A is a perspective view partially in section illustrating coil apparatus in an NMR imaging system, and FIGS. 1B-1D illustrate field gradients which can be produced in the apparatus of FIG. 1A. This apparatus is discussed by Hinshaw and Lent, "An Introduction to NMR Imaging: From the Bloch Equation to the Imaging Equation," Proceedings of the IEEE, Vol. 71, No. 3, Mar. 1983, pp. 338-350. Briefly, the uniform static field $B_0$ is generated by the magnetic comprising the coil pair 10. A gradient field $G(x)$ is generated by a complex gradient coil set which can be wound on the cylinder 12. An RF field $B_1$ is generated by a saddle coil 14. A patient undergoing imaging would be positioned along the Z axis within the saddle coil 14.

In FIG. 1B an X gradient field is shown which is parallel to the static field $B_0$ and varies linearly with distance along the X axis but does not vary with distance along the Y or Z axes. FIGS. 1C and 1D are similar representations of the Y gradient and Z gradient fields, respectively.

Figure 2:
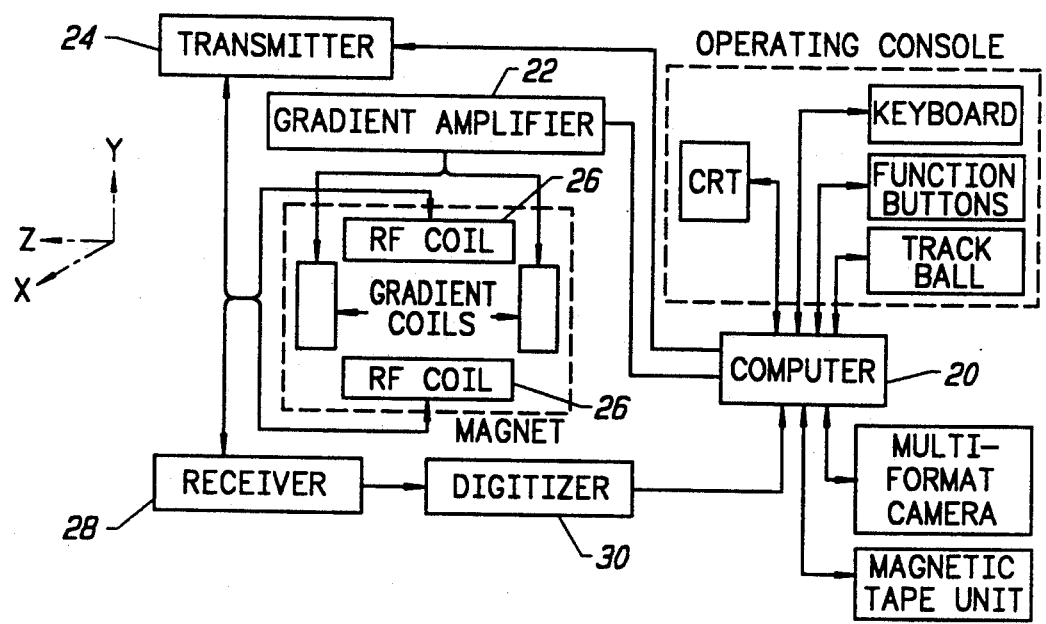
FIG. 2 is a functional block diagram of MRI imaging apparatus.

FIG. 2 is a functional block diagram of the imaging apparatus as disclose din NMR- A Perspective on Imaging, General Electric Company, 1982. A computer 20 is programmed to control the operation of the NMR apparatus and process FID signals detected therefrom. The gradient field is energized by a gradient amplifier 22, and the RF coils for impressing an RF magnetic moment at the Larmor frequency are controlled by the transmitter 24 and the RF coils 26. After the selected nuclei have been flipped, the RF coils 26 are employed to detect the FID signal which is passed to the receiver 28 and thence through digitizer 30 for processing by computer 20.

Figure 3:
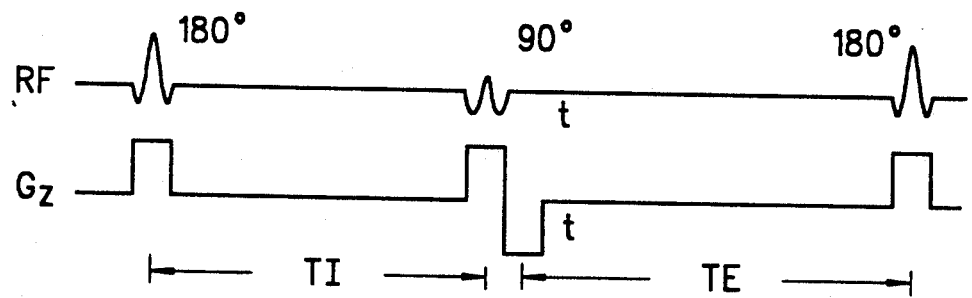
FIG. 3 illustrates a conventional basic pulse sequence for exciting a slab for projection imaging.

FIG. 3 is a graph illustrating applied RF pulses for a 180° flip angle and a 90° flip angle followed by a "time reversal" 180° pulse and the associated Z axis magnetic field gradient applied during application of the RF pulses. The illustrated pulses are conventional sinc pulses which have front and back lobes with a main RF pulse therebetween. From this representation, it can be seen that the angle of flip is proportional to the area under the pulse.

The present invention utilizes MR imaging signals to determine a characteristic of a moving fluid such as oxygen saturation of blood.

The determination of blood oxygen saturation finds application in assessing cardiac output, consumption of oxygen in perfused organs, and the severity of vascular shunts such as those found in congenital heart diseases. Available oximetry methods are based primarily on optical transmittance and reflectance differences between oxy- and deoxyhemoglobin. The resulting measure of blood oxygen saturation is the percentage of hemoglobin that is oxygenated, abbreviated as $\%HbO_2$. The poor penetration of tissue by light, however, limits the non-invasive monitoring of $\%HbO_2$ to superficially accessible regions. The determination of oxygen saturation in deep vascular structures currently must be made via direct sampling of the blood of interest.

Heretofore, investigators speculated that MRI measurement of T2 should be attainable; however, only qualitative in vivo signal variations attributed to the dependence of $T2_b$ on $\%HbO_2$ have been reported. Quantitative in vivo work demands a calibration of the $T2_b$ versus $\%HbO_2$ relationship for the specific experimental setup. The variations among experimental data fits for this relationship derived under a wide range of conditions with MR spectrometers demonstrate that the underlying mechanism is not adequately understood. In particular, the parametric fit of the $T2_b$ versus $\%HbO_2$ relationship appears to be sensitive to field strength and the time between refocusing pulses in a way not predicted by the Luz-Meiboom model used by most investigators. Only one known study has directly measure $T2_b$ for a wide range of $\%HbO_2$. This study examined rat blood on a 4.3-T spectrometer that refocused the signal every 2 msec. See Thulborn, et al. "Oxygenation Dependence of the Transverse Relaxation Time of Water Proteins in Whole Blood at High Field," Biophysica Acta 714, pp. 265-270, 1982. Thus, for in vivo $\%HbO_2$ estimation, this relationship must be experimentally quantified for conditions resembling as closely as possible those to be used for human in vivo studies.

Before performing this calibration, one must address a more basic challenge: accurate estimation of $T2_b$ in vivo in a manner consistent with the estimation of $HbO_2$. Difficulties that arise include (a) isolation of the blood signal of interest, (b) variation in signal strengths of blood at different TEs due to effects of flow such as wash-in of unexcited spins and dephasing, (c) artifacts due to motion (breathing and blood pulsatility), and (d) the poorer $B_0$ and $B_1$ homogeneity combined with weaker $B_0$ and $B_1$ fields available on wholebody imagers compared with those of spectrometers. This challenge is exacerbated because the vessels of interest include those of the mediastinum, where imaging conditions are the most demanding.

The origin of the $\%HbO_2$ effect on $T2_b$ is the irreversible dephasing of spins undergoing exchange and/or bounded diffusion through gradient fields in and around intact red blood cells. These gradients are established when $B_0$ is shifted for water inside the red blood cells due to the presence of paramagnetic deoxyhemoglobin. This frequency shift is proportional to the concentration of deoxyhemoglobin, found only therein directly reflecting blood oxygen saturation. Rapidly and regularly applying 180° pulses reduces the range of frequencies a spin experiences before it is "refocused" and hence reduces the degree to which this loss of coherence is irreversible.

The Luz-Meiboom model of relaxation in the presence of exchange between two sites at different frequencies is a good starting point for describing how this situation affects $T2_b$:

$$\frac{1}{T2_b} = \frac{1}{T2_0} + (P_A)(1-P_A)\tau_{ex}\left[\left(1-\frac{\%\,HbO_2}{100\%}\right)\alpha\omega_0\right]^2 \times \quad (1)$$

$$\left(1 - \frac{2\tau_{ex}}{\tau_{180}}\tanh\frac{\tau_{180}}{2\tau_{ex}}\right).$$

$T2_0$ is the T2 of fully oxygenated blood; $\tau_{ex}$ is a measure of the average time required for a proton to move between the two sites; $\omega_0$ is the resonant proton frequency; $\alpha$ is a dimensionless value related to the susceptibility of deoxyhemoglobin and the geometry of the erythrocyte, so that $\alpha\omega_0[1-(\%HbO_2/100\%)]$ can be considered the frequency difference between the two "sites" at which the protons exchange according to the Luz-Meiboom model; $P_A$ is the fraction of protons resident at one of the sites under exchange; $\tau_{180}$ is the interval between refocusing 180° pulses in the MR imaging sequence. The strength of the $\%HbO_2$ effect depends on field strength through the $\omega_0$ term, increasing quadratically with $B_0$ and therefore favoring the use of high-field-strength imagers for the study. The sensitivity of $T2_b$ to $\%HbO_2$ increases as $\tau_{180}$ increases, particularly when $\tau_{180}$ is on the order of $\tau_{ex}$. Although the Luz-Meiboom model was developed with the assumption of many short refocusing pulses for which $\tau_{180}$ is much less than T2, stimulations of the underlying exchange equations indicate that the model is equally value even when $\tau_{180}$ is equal to $T2_0$, as long as a $\alpha$ remains relatively small.

The present invention does not require all the degrees of freedom given in the Luz-Meiboom model. The invention requires parameterizing the T2 versus $\%HbO_2$ relationship in healthy subjects for a particular setup, not in exploring the details of the underlying mechanism as reflected by the parameters $\alpha$, $\tau_{ex}$, and $P_A$. These parameters can therefore be lumped into a single parameter K, which depends on the controllable variable $\tau_{180}\cdot\omega_0$ is also subsumed under K for one field strength. Thus, measurements of $T2_b$ for a range of $\%HbO_2$ will be fitted to a simplified Luz-Meiboom model for a small set of practical $\tau_{180}$ values:

$$\frac{1}{T2_b} = \frac{1}{T2_0} + K(\tau_{180}\cdot\omega_0)\left(1-\frac{\%\,HbO_2}{100\%}\right)^2. \quad (2)$$

The size of the $\%HbO_2$ effect increases with operating field strength. The examples herein are performed on a 1.5-T Signa unit (GE Medical systems, Milwaukee) which is among the highest-field-strength whole-body imagers that are widely used.

In Equation (2), the size of the $\%HbO_2$ effect is reflected in the parameters $t2_0$ and K (for sufficiently large $\tau_{180}$). When examining these parameters human blood is considered only under normal physiologic conditions-specifically, intact red blood cells suspended in plasma with a hematocrit around 45% and at 37° C. Temperature and hematocrit affect $T2_0$ and, to a lesser extent, K. Complete cell lysis eliminates the oxygen effect (K=0), while the development of methemoglobin in intact cells found in clots will increase K. Under normal conditions, $T2_0$ is approximately 220 msec ±30, per studies of oxygenated blood in a 1.4-T field. On the basis of Thulborn, et al. supra, $K(\tau_{180}\to\infty, B_0=1.5T)$ is approximately 40 sec$^{-1}$. $T2_b$ should be between 60 and 100 msec for sufficiently long $\tau_{180}$ when $\&HbO_2$ is about 50%, the minimum level that is likely of interest for studies of vascular blood. This indicates that $T2_b$ variations should be sufficient to reflect relatively small changes in $\%HbO_2$.

A second question is how fast one can refocus the signal while still realizing most of the $\%HbO_2$ effect (longer $\tau_{180}$ results in greater $\%HbO_2$ effect). More rapid refocusing (shorter $\tau_{180}$) is desirable to maintain spin coherence in the presence of complicated flow and to provide a sufficient range of TEs to accurately estimate $T2_b$. The full Luz-Meiboom model indicates that the dependence of $1/T2_b$ on $\tau_{180}$ is greatest for $\tau_{180}\approx\tau_{ex}$ and saturates as $\tau_{180}$ increases beyond about $5\tau_{ex}$. Ideally, one would use the value of $\tau_{180}$ at which this saturation begins. Independent of the above concerns, the minimum achievable $\tau_{180}$ is about 6 msec with the current experimental setup, limited by power absorption concerns and technical limitations of the radio frequency (RF) amplifier.

A reasonable $\tau_{180}$ is determined in part by the magnitude of the $\%HbO_2$ effect. To accurately measure TE, $\tau_{180}$ should be at most on the order of half of the $T2_b$ of interest. This suggests that one needs only consider a $\tau_{180}$ of less than 50 msec. Where the saturation point for the effect of $\tau_{180}$ lies is not clear in the literature. Nonetheless, considering values of $\tau_{180}$ only up to 50 msec appears reasonable. From the data fits of Thulborn, et al. (determined primarily from data acquired at 4.3 T), one would not expect K to vary much with $\tau_{180}$ over the range of practical interest (>6 msec). From experiments performed primarily at 1.4T, K should increase significantly as $\tau_{180}$ increases from 6 to 50 msec and should then level off slowly for further increases in $\tau_{180}$.

Figure 4:
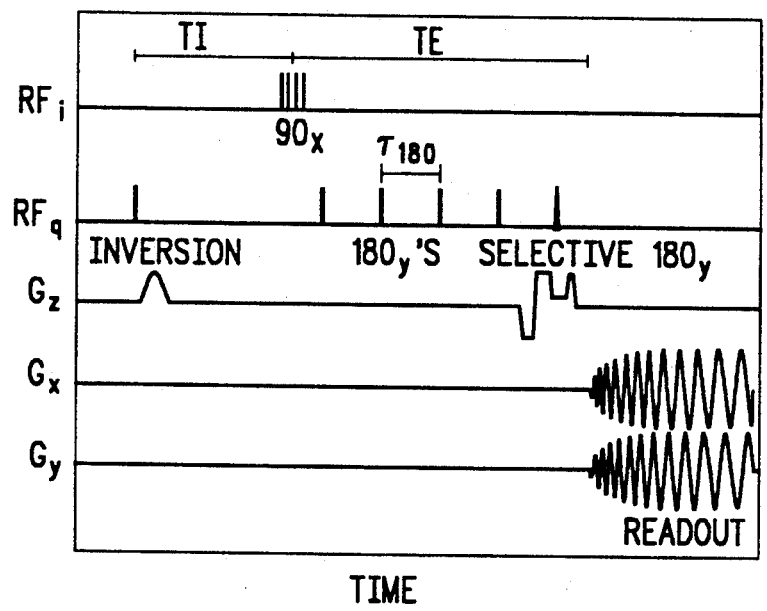
FIG. 4 is a pulse sequence for the in vivo estimation of $T2_b$ in accordance with one embodiment of the invention.

For spectrometer studies of blood, CPMG (Carr-Purcell-Meiboom-Gill) sequence is used most often to measure $T2_b$. A version of this lies at the heart of the sequence herein; however, several modifications are made to address the challenges of the in vivo environment. The resulting sequence (FIG. 4) is that originally introduced for the purpose of flow-independent angiography augmented to include (a) spatial selectivity without wash-in effects, (b) reduced flow dephasing, and (c) faster image acquisition (to minimize, where necessary, effects of body motion).

To suppress fat signal, the sequence beings with a short T1 inversion recover (STIR) sequence (TI=120 msec) followed by a frequency-selective 90° pulse that excites only the water protons. Fat is often found surrounding vessels and just under the skin. By eliminating its signal, one can minimize its contribution to signal measure in the vessel caused by partial-volume averaging and by blurring of fat signal (which occurs when one uses time-varying gradients of relatively long duration at data acquisition). Furthermore, artifacts from the normally high-signal-intensity fat in the chest wall that are due to breathing are suppressed. STIR minimizes the fat signal in the longitudinal magnetization at excitation, which as the added advantage of minimizing spurious signal from fat generated by the imperfect hard refocusing pulses that follow. Frequency-selective excitation provides additional fat suppression because it is difficult to properly tune T1 to achieve the desired level of suppression.

After excitation, the transverse magnetization is refocused every $\tau_{180}$ msec by rectangular 180° pulses. This pulse train establishes the constant refocusing interval required for accurate $T2_b$ estimation in the Luz-Meiboom model. It also restores the coherence of spins dephased because of flow through $B_0$ inhomogeneities. To minimize flow dephasing, spoiling gradients during the refocusing train are not used; however, this could lead to the propagation of spurious signals. One can generate strong spurious signals and lose significant amounts of desired signal because of errors in the axis and amplitude of flip angles, particularly when there are many pulses in the refocusing train. To minimize the effects of these errors, caused by $B_0$ and $B_1$ inhomogeneities, the sign of the 180° pulses is varied according to the MLEV pattern whenever there are at least four pulses in the train. This pattern of sign variation is more robust than the standard CPMG pattern in the presence of $B_0$ inhomogeneities; however, under this scheme one should acquire signal only after $2^n$ pulses, where n is an integer.

As the first step in isolating blood signal by spatial location, the final refocusing 180° pulse is section selective and is bracketed by a pair of spoiling gradients to dephase the out-of-section signal. These gradients and the section-select gradient are flow compensated. Effects of wash-in and of the physical dispersion of tagged spins on blood signal are avoided because this is the only spatially selective pulse in the sequence and it is as close as possible to the data acquisition.

Finally, signal from the section is spatially encoded during data acquisition. Two variations are implemented. In the more standard case, the two-dimensional Fourier transform (2DFT) encoding of the original flow independent angiography sequence is used. To minimize flow dephasing with this arrangement, all spatial-encoding gradients (notably the phase-encoding lobe and the dephasing lobe of the readout gradient) are kept compact and close to the data acquisition interval. In the second case, illustrated in FIG. 4, spiral gradients rapidly cover k space during data acquisition. See Meyer, et al. "A Comparison of Fast Spiral Sequences for Cardiac Imaging and Angiography" (abstr); in Book of abstracts: Society of Magnetic Resonance in Medicine 1990; 403. This version is useful when the duration of image acquisition is an issue. For instance, when imaging the chest, acquiring an entire image in a single breath hold minimizes motion effects. For this gain, poorer signal-to-noise ratios (S.Ns) and greater sensitivity to blurring caused by $B_0$ inhomogeneity must be accepted. Each spiral readout begins at the center of k space and at the center of the spin echo to minimize the effects of flow and $B_0$ inhomogeneities. Further more, the spiral trajectory has well-behaved gradient moments, maintaining flow coherence throughout the acquisition.

Timing of the data acquisitions can decrease sensitivity to the presence of flow. To prevent loss of coherence in subsequent echoes due to flow effects, signal is acquired at only one TE per excitation. To measure T2, we repeat the sequence at three to four different TEs. To minimize effects of flow pulsatility, the sequence is gated to the cardiac cycle so that readout occurs in the same period of diastole independent of the selected TE. Data are acquired once every other heartbeat to maximize S/N per unit imaging time and to allow adequate T1 recovery to minimize effects of variable R-R intervals. Extra rectangular 180° pulses are included after acquisition for all but the longest TE of interest to ensure that the effective recovery time ($TR_e$) is independent of the TE at which the signal is received.

While the resulting sequence is rather involved, each element is chosen for its simplicity and/or availability with the objective of expeditious implementation. Potential variations include the use of crafter pulses for frequency-selective excitation or more robust refocusing as well as alternative rapid acquisition strategies.

As noted earlier, all experiments were performed on a 1.5-T Signa unit. The system includes superconducting and resistive shims with which field variations of less than 20 Hz can be achieved over a 20-cm field of view in a uniform phantom. No supplementary shimming was done for individual experiments. Good shims minimize flow dephasing and diffusion effects during the refocusing train, as well as blurring when data are acquired with the spiral gradients. $B_1$ amplitudes are limited to about 625 Hz. The system is equipped with 10-mT/m gradients with which one can generate a $192 \times 192$ image of a 24-cm field of view in eight 40-msec spiral acquisitions. See Meyer, et al., supra. Shielded gradient coils minimize eddy current effects during such acquisitions. All cardiac gating was performed with a plethysmography.

EXPERIMENT 1

Bias in T2 Measurement

Before experimenting on blood, demonstration that the features added to the sequence to address in vivo issued do not affect T2 estimation is made. Also shown is that the sequence does not introduce measurement bias in the presence of flowing material. The phantom used in this study was plastic tubing with an inner diameter of 0.6 cm containing a manganese chloride solution with a T1 of approximately 1,200 msec and a T2 of approximately 120 msec. The tubing runs through a pump and settling system so that steady flow of fluid can be achieved. The phantom is a crude model of blood in a vessel. The tubing runs parallel to the main field in the magnet bore to minimize susceptibility effects, was measured with the following sequences:

Sequence A: a standard multi-echo 2DFT sequence with a TR of 2,000 msec and TEs of 48, 96, 144, and 192 msec, acquiring axial sections through the tube; $TR_e = 1,808$ msec.

Sequence B: a simplified version of the proposed sequence with only a rectangular excitation pulse, the train of hard refocusing pulses, each bracketed by spoiling gradients, and a 2DFT phase encoding and readout to produce coronal projection images. One TE is acquired per excitation; $\tau_{180} = 24$ msec; TE = 48, 96, and 192 msec; $TR_e = 1,808$ msec for each image. This sequence is also repeated with a $\tau_{180}$ of 24 msec; TEs of 24, 48, 96, 192, and 384 msec; and a $TR_e$ of 2,000 msec.

Sequence C: the complete proposed sequence, including STIR, frequency-selective excitation, the refocusing train without spoiling gradients, a final spatially selective pulse, and spiral gradients during data acquisition to generate axial sections. $\tau_{180} = 24$ msec; TE = 24, 72, 120, 216, and 408 msec; TR = 2,000 msec. Extra refocusing pulses after data acquisition make the effective T1 recovery time $TR_e$ 1,592 msec for each TE.

The effects of flow on $T2_b$ measurement were examined with sequence C in the presence of steady flows of 9, 18, and 30 cm/sec. For a flow of 18 cm/sec, this sequence was repeated with $\tau_{180}$ values of 6 and 12 msec to ensure that varying the refocusing rate in the presence of flow does not bias $T2_b$ measurements.

In these and all later experiments, T2 values were estimated with a weighted least-squares fit of a monoexponential decay to the average signal intensities in a small region of the phantom.

TABLE 1

Table 1 summarizes the T2 estimates:
Estimates of T2 of Phantom under Various Experimental Conditions

| Sequence | $\tau_{180}$(msec) | Flow Rate (cm/sec) | T2(msec) |
|---|---|---|---|
| A | 48 | 0 | 95 |
| B | 48 | 0 | 121 |
| B | 24 | 0 | 122 |
| C | 24 | 0 | 121 |
| C | 24 | 9 | 116 |
| C | 24 | 18 | 117 |
| C | 24 | 28 | 115 |
| C | 12 | 18 | 115 |
| C | 6 | 18 | 120 |

In all cases, monoexponential decay fit the data well. The cases, monoexponential decay fit the data well. The standard error in repeat measurements of T2 was about 3 msec. The commercial multi-echo sequence (A) yielded significantly smaller T2 estimates than the two versions (B and C) of the proposed sequence. When we repeated the measurements with the commercial sequence but used only a single echo per acquisition and a very long TR, we obtained T2 values comparable with those found with sequences B and C. Hence, the commercial multi-echo sequence appears to introduce a biasing error. Further investigation of this problem was beyond the scope of this study; however, potential sources of such errors in multi-echo sequences on imagers have bene investigated by others. Both the simplified version (B) and the complete version (C) of the proposed sequence yielded the same T2 values for stationary fluid. T2 measurements with sequence C were relatively independent of velocity for steady flows. Similarly, varying $\tau_{180}$ in the presence of steady flow did not affect T2 measurements. Thus, the proposed sequence seems to reflect true transverse relaxation under various conditions. These results also add credence to the use of the relationship between $T2_b$ and %HbO$_2$-established with in vitro experiments in which stationary blood was imaged with sequence B-in estimating %HbO$_2$ levels of flowing blood in vivo from $T2_b$ determined with sequence C.

EXPERIMENT 2

In vitro Calibration of $T2_b$ versus %HbO$_2$

To establish a quantitative relationship between $T2_b$ and %HbO$_2$, the T2s of human blood oxygenated to varying degrees were measures for a practical range of $\tau_{180}$ values. The parameters K and $T2_b$ of Equation (2) were determined by a least-squares fit to the resulting data.

Blood was drawn via venipuncture form five healthy volunteers after their informed consent was obtained. In some cases, the subject's arm was cooled in water (18° C.) to reduce oxygen saturation of the venous blood. No chemicals were added to further reduce %HbO$_2$. The samples were citrated and then aerated to varying levels of %HbO$_2$ (as measured with a reflectance oximeter [american Optical, Buffalo]), starting at the level at which the blood was drawn. The samples were then stored in evacuated 5-mL glass tubes in which the %HbO$_2$ levels could be maintained for several hours. This was confirmed by remeasuring the HbO$_2$ of each sample after the $T2_b$ measurements. Hematocrit was also measured at this time.

Data for the $T2_b$ measurements were acquired within 2 hours after the original blood drawing. Before imaging, sets of blood-containing tubes were immersed in an insulated bath of water doped with MnCl$_2$ (T2 < 2 msec) at 37° C. to minimize B$_0$ inhomogeneity due to susceptibility and to maintain the blood at body temperature throughout the experiment. A head coil was used for excitation and signal reception. For greater S/N and reduced susceptibility effects, sequence B, the simplified version described in the previous section, was used to measure the $T2_b$ values. Specifically, $T2_b$ values were measured for $\tau_{180}$ values of 6, 12, 24 and 48 msec. For each $\tau_{180}$, signals were acquired at Tes ranging from 24 to 384 msec; TR$_e$ was 2,000 msec. Before each set of measurements, the samples were agitated to minimize settling effects. Sequence C was also run in a subset of the experiments to check for any differences when imaging blood.

The blood samples used in this experiment has HbO$_2$ levels ranging from 30% to 96%. Direct %HbO$_2$ measurements in the samples, obtained before and after $T2_b$ measurements, differed on average by about 2%. Hematocrits in different subjects ranges from 42% to 47%. The integrity of the erythrocytes was maintained throughout the study, on the basis of examination of centrifuged sampled.

Figure 5:
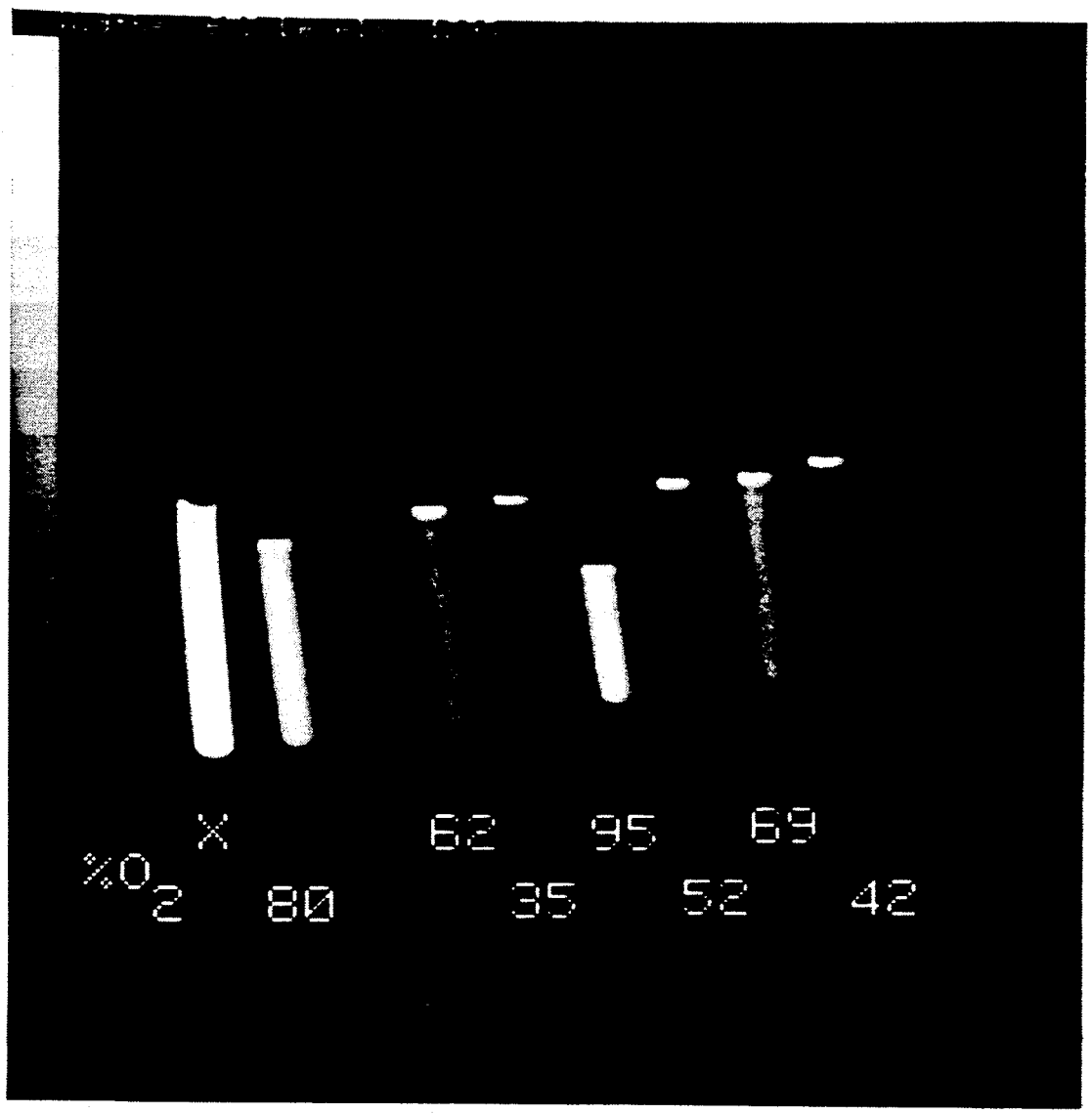
FIG. 5 is a projection image of blood samples.
Figure 6A:
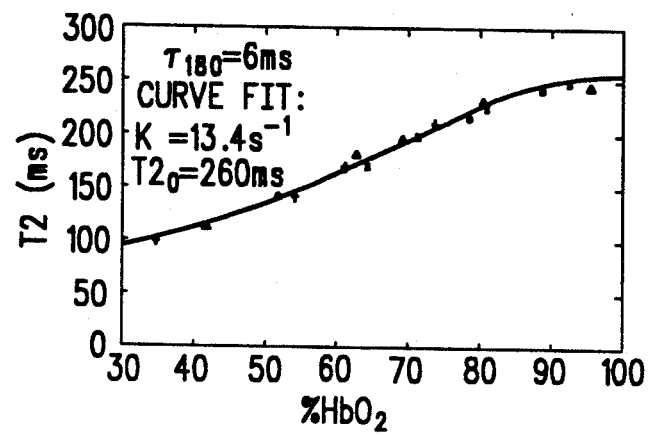
FIGS. 6A, 6B, 6C and 6D are plots of $T2_b$ versus $\%HbO_2$ for different spacings of refocusing pulses.
Figure 6B:
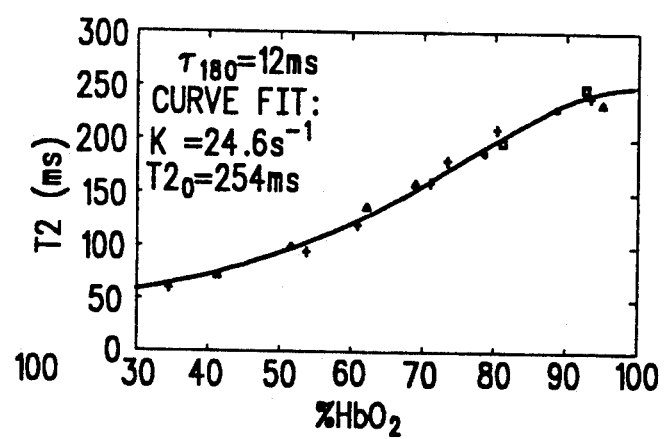
Figure 6C:
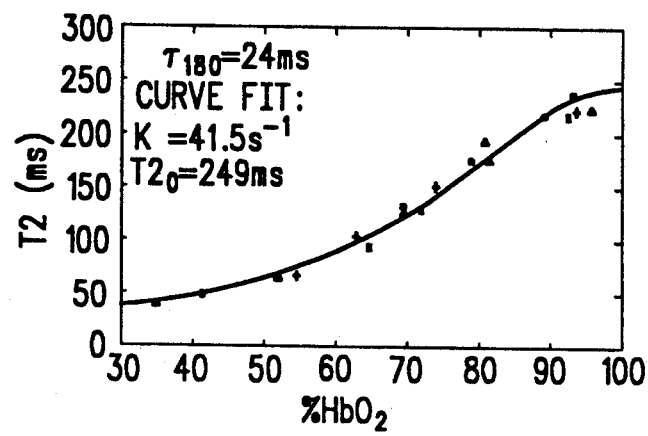
Figure 6D:
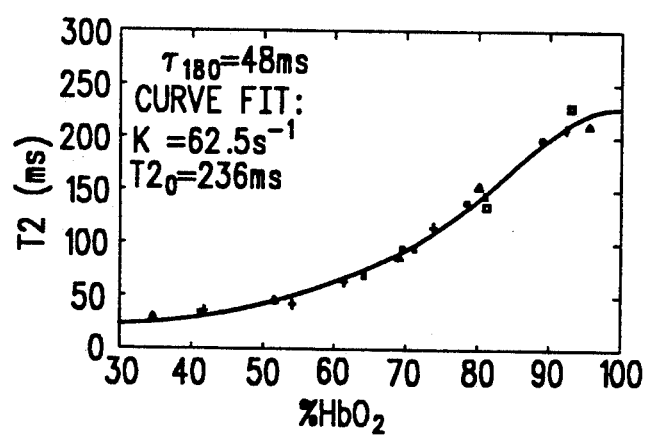

FIG. 5 depicts one of the images used for the estimation of $T2_b$. The variation in intensity with oxygen weighted image. The $T2_b$ of each sample was estimated from the average signal intensity determined in a small square region at about the center of the sample.

Transverse relaxation of the blood is well described by monoexponential decay. Most errors in fitting this model to measured signal intensities can be attributed to random noise in the raw data, on the basis of the results of $\chi^2$ tests. The resulting estimates of $T2_b$ are plotted in FIG. 6 as a function of the %HbO$_2$ measured for the corresponding samples. Standard errors in the estimates of $T2_b$, based on propagation of random noise in the raw images, range from approximately 0.5 msec for a $T2_b$ of 30 msec to 5 msec for a $T2_b$ of 250 msec. For each $\tau_{180}$, we estimated K and $T2_0$ via a least-squares fit of Equation (2) to the data, weight to allow for the expected error in the $T2_b$ values. The resulting parametric values and the corresponding curve firs are presented in FIG. 3.

Equation (2) provides a reasonable fit to the data. There is strong evidence that K varies with $\tau_{180}$ over the range studied (6–48 msec), in general concurrence with spectrometry studies at about the same field strength however, the limited data would yield somewhat lower estimates of $\tau_{ex}$ (3–5 msec). As discussed above, the minimum $\tau_{180}$ value for which K is close to its maximum should be used. The larger K reflects a greater %HbO$_2$ effect, minimizing the propagation of error from the $T2_b$ measurement to the %HbO$_2$ estimate. Earlier work, as well as current results, indicates that the influence of $\tau_{180}$ on K decreases as $\tau_{180}$ increases beyond approximately 24 msec, although we still see a significant change from 24 to 48 msec. Using a $\tau_{180}$ of 24 msec gives a reasonable trade-off between maximizing K and minimizing flow effects and provides a sufficient range of TEs for estimating $T2_b$.

Under this arrangement, the standard error in predicting %HbO$_2$ from $T2_b$ measured in vitro is about 2.5% over the range of clinical interest (%HbO$_2$<90%). The reflectance oximeter used as a standard is accurate to ±2% in this range, so this reference is potentially a major source of error. For clinical work, accuracy to within 3% is generally acceptable. For the %HbO$_2$ range of arterial blood (>90%), the model suggests that T2$_b$ is much less sensitive to %HbO$_2$ in general, predicting poorer accuracy for such estimates. This may not be a major concern in clinical work because one often simply assumes that arterial blood is fully oxygenated for one uses values of arterial %HbO$_2$ measured in surface regions with a pulse oximeter. Hence, the current level of accuracy of %HbO$_2$ estimates would be practically useful if it could be achieved in vivo.

Of particular interest is the effect of individual differences in hematocrit. There is evidence that 1/T2$_0$ varies linearly with hematocrit while K varies quadratically. On the basis of these results, for hematocrits ranging from 30% to 50% (an extreme range encompassing many pathologic conditions), changes in K would introduce at most a 3% error in %HbO$_2$ if not accounted for, while changes in T2$_0$ would yield substantially greater errors. Estimates of K for a given $\tau_{180}$ were consistent from subject to subject, while there was weak evidence of individual differences in the parameter T2$_0$ (although these differences did not appear to correlate with the small variations in hematocrit).

EXPERIMENT 3

In vivo Studies

Using the complete in vivo sequence (sequence C), T2$_b$ was measured in several vessels of clinical interest-primarily the aorta, superior vena cava, and pulmonary trunk-sin several health volunteers (with their informed consent). The signals from these vessels were isolated by acquiring an axial section through the pulmonary trunk while the subject lay prone, with a circular surface coil 18 cm in diameter beneath the chest to receive the signal. With use of spiral gradients during readout and reception of signal every other heartbeat during diastole, an image could be acquired in 16 heartbeats, during which the subjects held their breath. This breath-hold interval is quite reasonable for the current study of healthy subjects; however, further development may be required to reduce the interval in patient studies. The resulting image has a resolution of 1.7×1.7×10 mm. To estimate T2$_b$, four to five images were acquired at TEs ranging from 24 to 408 msec. For most subjects, the signal was refocused every 24 msec. The experiments were repeated using $\tau_{180}$ values of 6 and 12 msec in three subjects to demonstrate the effect of $\tau_{180}$ in vivo. T2$_b$ values were also estimated with 2DFT data acquisition for vessels in an axial section of the arm and for the descending aorta and inferior vena cava in an axial section of the abdomen in individual subjects.

Figure 7:
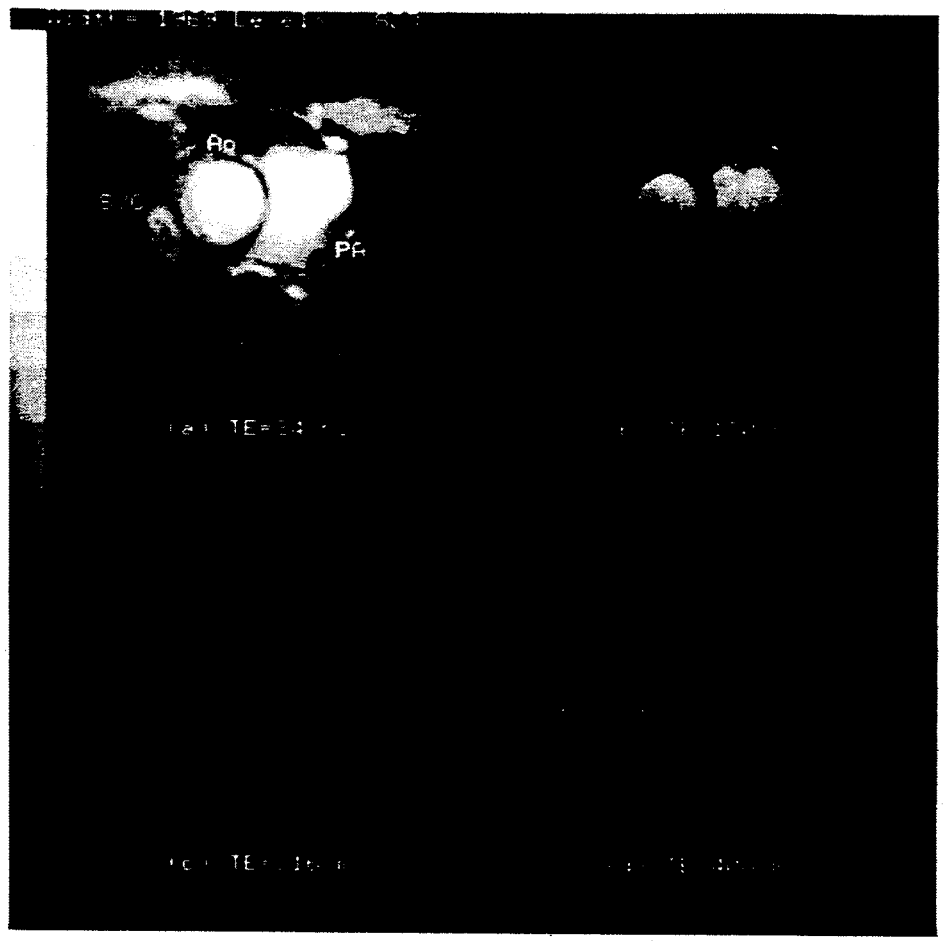
FIG. 7 is images used for the estimation of $T2_b$ in vivo.

FIG. 7 shows a set of images of an axial section through the pulmonary trunk in one volunteer, acquired at various TEs. These were used to estimate T2$_b$ values in the aorta, superior vena cava, and pulmonary trunk. One can observe the blurring in off-resonance regions caused by susceptibility effects (primarily at the chest wall and where pulmonary arteries enter the lungs) when the signal is acquired with spiral gradients of relatively long duration. Nonetheless, the signals in the vessels of interest are well isolated; indeed, virtually no flow dephasing or wash-in effects are observed in the blood signal, even at the late TEs.

The T2$_b$ estimates for this subject and those for several other subjects, determined with the same protocol, are listed in Table 2.

TABLE 2

| | | | %HbO$_2$ Estimates from Measurements of T2$_b$ in Vivo | | | | | |
|---|---|---|---|---|---|---|---|---|
| | | | Aorta | | Superior Vena Cava | | Pulmonary Trunk | |
| Subject | T2$_0$(msec)* | $\tau_{180}$(msec) | T2$_b$(msec) | %HbO$_2$ | T2$_b$(msec) | %HbO$_2$ | T2$_b$(msec) | %HbO$_2$ |
| 1 | 224 | 6 | 223 | 97* | 185 | 74 | 202 | 81 |
| | | 24 | 220 | 96 | 138 | 74 | 161 | 80 |
| 2 | 243 | 12 | 242 | 97* | 175 | 75 | 194 | 79 |
| | | 24 | 230 | 93 | 155 | 76 | 180 | 81 |
| 3 | 214 | 12 | 213 | 97* | 154 | 73 | 162 | 75 |
| | | 24 | 196 | 90 | 126 | 72 | 147 | 77 |
| 4 | 196 | 24 | 194 | 97* | 139 | 78 | 122 | 73 |
| 5 | 277 | 24 | 274 | 97* | 171 | 77 | 186 | 79 |

*T2$_0$ chosen so that %HbO$_2$ = 97% for blood in aorta for minimum $\tau_{180}$ used.

Monoexponential decay provides a good fit to the data when estimating the T2$_b$ values, although errors are generally greater than those due to random noise alone. Sources of residual error may include dephasing due to complicated flow, the presence of spurious signals, and variations in average R-R interval and breath-hold position between images with different TEs.

These in vivo results reflect, at least qualitatively, the in vitro results. For each subject, venous blood (pulmonary turn, and vena cava) clearly has a shorter T2 than arterial blood (aorta). In four of the five subjects studies, blood in the pulmonary trunk had a longer T2 than that in the superior vena cava. One might infer that the %HbO$_2$ in the pulmonary trunk is greater. Whether this is normally true for healthy subjects is not clear from the medical literature. The range of T2$_b$ values is certainly within that measure in vitro. Comparing the T2$_b$ values measured with $\tau_{180}$ values of 6 and 24 msec in one subject shows a clearly significant decrease in T2$_b$ for venous blood at the longer refocusing time, as expected on the basis of the in vitro results. When the difference in $\tau_{180}$ values was less (12 vs 24 msec), the results were less conclusive, since the T2$_b$ of arterial blood changes almost as much as that of venous blood.

Before one can estimate %HbO$_2$ from the measured T2$_b$ values, the question remains as to the appropriate parametric values to use in Equation (2). Without evidence to the contrary, it is assumed that the values of K estimated from in vitro data are equally valid for vivo studies. In choosing T2$_0$, there are several considerations. In healthy subjects at rest, one would expect that %HbO$_2$ for aortic blood should always be about 97%. This implies that T2$_0$ should be only slightly greater than T2$_b$ in the aorta. If we fix T2$_0$ to the average value obtained form the vitro work, we can expect large errors in estimates of %HbO$_2$ for arterial blood (e.g., estimated %HbO$_2$ is 83% for a T2$_b$ of 194 msec in subject 4, if T2$_0$ is 250 msec) or meaningless results if T2$_b$ is greater than T2$_0$. If we use measurements of T2$_b$ in the aorta to estimate T2$_0$, we are clearly making assumptions about %HbO$_2$ in the arteries and hence have no predictive power for these vessels. For expediency, we use the latter approach to study %HbO$_2$ estimation in the venous blood; however, this clearly unsatisfactory state reinforces the earlier conclusion indicating the need for further study of factors affecting T2$_0$. The results are listed in Table 2. The influence of T2$_0$ is reduced for the T2 of venous blood; hence, the difference between estimates of %HbO$_2$ obtained with the above two approaches for determining T2$_0$ is on average about 3%. Except for subject 5, the %HbO$_2$ estimates would be reduced with a T2$_0$ of 250 msec.

SUMMARY

There has been described a method of determining characteristics of a moving fluid using magnetic resonance image signals. While the invention has been described with reference to oxygen saturation of blood, the examples are illustrative of the invention and are not to be construed as limiting the invention. For example, the invention can be used in determining characteristics of spinal fluid based on T2 measurements. Thus, various modifications and applications may occur to those skilled in the art without departing from the true spirit and scope of the invention as defined by the appended claims.

What is claimed is:

1. A method of determining a characteristic of a moving fluid based on measurements of spin-spin relaxation time of the fluid comprising the steps of
    a) placing said moving fluid in a static magnetic field (B$_0$) along a first axis (z),
    b) applying an excitation RF signal to said moving fluid thereby establishing transverse nuclei spins,
    c) applying a plurality (0,1,2, ... N) of 180° refocusing pulses to said moving fluid with said pulses being equally spaced, the number and spacing of said pulses determining echo time,
    d) applying after said plurality of 180° refocusing pulses a slice selective pulse (that is slice selective), the time between said slice selective pulse and an echo being constant,
    e) detecting signals from said nuclei spins,
    f) determining the spin-spin relaxation time of said nuclei spins from said signals, and
    g) determining said characteristic from said spin-spin relaxation time.

2. The method as defined in claim 1 wherein said moving fluid is blood and said characteristic is oxygen saturation of the blood.

3. The method as defined in claim 2 wherein the relationship of measured spin-spin relaxation time, T2$_b$, to calculated oxygen saturation of blood, %HbO$_2$, is given by:

$$\frac{1}{T2_b} = \frac{1}{T2_0} + K(\tau_{180} \cdot \omega_0)\left(1 - \frac{\% HbO_2}{100\%}\right)^2.$$

where
T2$_0$ is the spin-spin relaxation time of fully oxygenated blood, $\tau_{180}$ is time between successive pulses in said plurality of 180° refocusing pulses,
$\omega_0$ is the resonant nuclei frequency, and
K is a constant.

4. The method as defined by claim 3 wherein step b) includes at least one of i) applying an inversion pulse, then applying a magnetic gradient (Gz) along said first axis, and ii) applying a frequency selective 90° pulse that excites water protons, thereby suppressing signals from fat.

5. The method as defined by claim 3 wherein step c) includes applying a pair of spoiling gradients with said last pulse to dephase any out of section signal.

6. The method as defined by claim 3 wherein step d) includes spatially encoding the signals using two-dimensional Fourier transform encoding.

7. The method as defined by claim 3 wherein step d) includes spatially encoding the signals using spiral gradients in k space during data acquisition.

8. The method as defined by claim 1 wherein step b) includes applying an inversion pulse, then applying a magnetic gradient (Gz) along said first axis, and then applying a frequency selective 90° pulse that excites water protons, thereby suppressing signals from fat.

9. The method as defined in claim 1 wherein step c) includes applying a pair of spoiling gradients with said last pulse to dephase any out of section signal.

10. The method as defined in claim 1 wherein step d) includes spatially encoding the signals using two-dimensional Fourier transform encoding.

11. The method as defined in claim 1 wherein step d) includes spatially encoding signals using spiral gradients in k space durnig data acquisition.

12. Apparatus for determining a characteristic of a moving fluid based on measurements of spin-spin relaxation time of the fluid comprising
    a) means for establishing a static magnetic field (B$_0$) through said fluid along a first axis (z),
    b) means for applying an inversion RF signal to said moving fluid thereby establishing transverse nuclei spins,
    c) means for applying a plurality of 180° refocusing pulses to said moving fluid with said pulses being equally spaced,
    d) means for applying a slice selective pulse after said plurality of 180° pulses, the time between said slice selective pulse and an echo being constant,
    e) means for detecting free induction decay signals from said nuclei spins,
    f) means for determining the spin-spin relaxation times of said nuclei spins from said signals, and
    g) means for determining said characteristic from said spin-spin relaxation time.

13. Apparatus as defined by claim 12 wherein said moving fluid is blood and said characteristic is oxygen saturation of blood, the relationship of measured spin-spin relaxation time, T2$_b$, to calculated oxygen saturation of blood, %HbO$_2$, is given by:

$$\frac{1}{T2_b} = \frac{1}{T2_0} + K(\tau_{180} \cdot \omega_0)\left(1 - \frac{\% HbO_2}{100\%}\right)^2.$$

where
T2$_0$ is the spin-spin relaxation time of fully oxygenated blood, $\tau_{180}$ is time between successive pulses in said plurality of 180° refocusing pulses, $\omega_0$ is the resonant nuclei frequency, and K is a constant.

14. Apparatus as defined by claim 13 wherein said means for detecting free induction decay signals includes means for spatially encoding the signals using two-dimensional Fourier transform encoding.

15. Apparatus as defined by claim 14 wherein said means for detecting free induction decay signals includes means for applying spiral gradients in k space during data acquisition.

* * * * *

UNITED STATES PATENT AND TRADEMARK OFFICE
CERTIFICATE OF CORRECTION

PATENT NO. : 5,233,991
DATED : August 10, 1993
INVENTOR(S) : Graham A. Wright

It is certified that error appears in the above-indentified patent and that said Letters Patent is hereby corrected as shown below:

Column 1, after the title, insert the following paragraph:

--This invention was made with Government support under contract No. HL39478 awarded by the National Institutes of Health. The Government has certain rights in this invention.--

Signed and Sealed this

Thirteenth Day of December, 1994

Attest:

BRUCE LEHMAN

Attesting Officer

Commissioner of Patents and Trademarks